US011896401B2

(12) United States Patent
Galdi

(10) Patent No.: US 11,896,401 B2
(45) Date of Patent: *Feb. 13, 2024

(54) PERSONAL HEALTHCARE DEVICE

(71) Applicant: Helo Corp., San Francisco, CA (US)

(72) Inventor: Fabio Galdi, Santa Clara, CA (US)

(73) Assignee: Helo Corp., San Francisco, CA (US)

(*) Notice: Subject to any disclaimer, the term of this patent is extended or adjusted under 35 U.S.C. 154(b) by 178 days.

This patent is subject to a terminal disclaimer.

(21) Appl. No.: 17/142,093

(22) Filed: Jan. 5, 2021

(65) Prior Publication Data

US 2021/0228159 A1 Jul. 29, 2021

Related U.S. Application Data

(63) Continuation of application No. 15/972,787, filed on May 7, 2018, now Pat. No. 10,912,519.

(Continued)

(51) Int. Cl.
*A61B 5/00* (2006.01)
*A61B 5/024* (2006.01)
(Continued)

(52) U.S. Cl.
CPC .......... *A61B 5/7267* (2013.01); *A61B 5/0013* (2013.01); *A61B 5/0205* (2013.01); *A61B 5/02433* (2013.01); *A61B 5/02438* (2013.01); *A61B 5/1118* (2013.01); *A61B 5/1455* (2013.01); *A61B 5/14532* (2013.01); *A61B 5/681* (2013.01); *A61B 5/7246* (2013.01); *A61B 5/7278* (2013.01); *A61B 5/742* (2013.01); *G16H 20/30* (2018.01); *G16H 40/67* (2018.01); *G16H 50/20* (2018.01); *G16H 50/30* (2018.01);
(Continued)

(58) Field of Classification Search
CPC ... A61B 5/7267; A61B 5/0013; A61B 5/0205; A61B 5/02433; A61B 5/02438; A61B 5/1118; A61B 5/14532; A61B 5/1455; A61B 5/681; A61B 5/7246; A61B 5/7278; A61B 5/742; A61B 5/0002; A61B 5/02; A61B 5/021; A61B 5/024; A61B 5/165; A61B 5/4815; A61B 2562/0233; A61B 2562/0238; G16H 20/30; G16H 40/67; G16H 50/20; G16H 50/30
See application file for complete search history.

(56) References Cited

U.S. PATENT DOCUMENTS 6,134,458 A * 10/2000 Rosenthal ............ A61B 5/0059
600/310
2016/0113526 A1* 4/2016 Nageshwar .......... A61B 5/7278
600/407

(Continued)

*Primary Examiner* — Eric F Winakur
*Assistant Examiner* — Abid A Mustansir
(74) *Attorney, Agent, or Firm* — Antonio Papageorgiou; Lombard & Geliebter LLP

(57) ABSTRACT

A method and system for measuring personal health, the method comprising detecting a photoplethysmograph (PPG) wave, the PPG wave generated based on a combination of infra-red and red lights, transmitting the PPG wave to a server, the server processing the PPG wave to infer biometric statistics based on machine learned correlations generated from a training set of PPG waves and biometric data, receiving the biometric statistics from the server, and generating display data based on the biometric statistics.

20 Claims, 16 Drawing Sheets

Related U.S. Application Data

(60) Provisional application No. 63/088,223, filed on Oct. 6, 2020, provisional application No. 62/501,995, filed on May 5, 2017.

(51) Int. Cl.
| | |
|---|---|
| *G16H 50/20* | (2018.01) |
| *G16H 20/30* | (2018.01) |
| *A61B 5/0205* | (2006.01) |
| *A61B 5/11* | (2006.01) |
| *A61B 5/145* | (2006.01) |
| *A61B 5/1455* | (2006.01) |
| *G16H 40/67* | (2018.01) |
| *G16H 50/30* | (2018.01) |
| *A61B 5/16* | (2006.01) |
| *A61B 5/02* | (2006.01) |
| *A61B 5/021* | (2006.01) |

(52) U.S. Cl.
CPC ............... *A61B 5/0002* (2013.01); *A61B 5/02* (2013.01); *A61B 5/021* (2013.01); *A61B 5/024* (2013.01); *A61B 5/165* (2013.01); *A61B 5/4815* (2013.01); *A61B 2562/0233* (2013.01); *A61B 2562/0238* (2013.01)

(56) References Cited

U.S. PATENT DOCUMENTS

| | | | |
|---|---|---|---|
| 2016/0242683 A1* | 8/2016 | Ishiguro | G01N 21/4795 |
| 2016/0302706 A1* | 10/2016 | Richards | A61B 5/0002 |
| 2017/0079578 A1* | 3/2017 | van den Broek | A61B 5/6801 |

\* cited by examiner

1.LED

| | | Wavelength | Attributes | Name |
|---|---|---|---|---|
| LED Spec | | | | LED640 |
| | LED2 | 940nm | infrared | LED940 |
| | LED3 | 1300nm | infrared | LED1300 |
| | LED4 | 1550nm | infrared | LED1550 |

| | Monitoring project | LED combination | | |
|---|---|---|---|---|
| LED function | Heart rate | LED640 + LED940 + LED1300 + LED1550 | | |
| | Blood oxygen | LED640 + LED940 | | |
| | Blood sugar | LED640 + LED940 + LED1300 + LED1550 | | |

Fig. 6B

PERSONAL HEALTHCARE DEVICE

CROSS REFERENCE TO RELATED APPLICATIONS

The application is a continuation-in-part of U.S. patent application Ser. No. 15/972,787, entitled "PERSONAL HEALTHCARE DEVICE," filed on May 7, 2018, which claims the benefit of U.S. Provisional Patent Application No. 62/501,995, filed on May 5, 2017, and also claims the benefit of U.S. Provisional Patent Application No. 63/088,223, filed on Oct. 6, 2020, the disclosure of each of which is hereby incorporated by reference in its entirety.

BACKGROUND OF THE INVENTION

The present application relates to wearable healthcare devices and more particularly devices that gather data and monitor a user's biometrics.

Although wearable biometric monitors are available, most have limited functionality. For instance, most are limited to measuring steps taken/distance covered and heart rate. Those interested in a more in-depth profile of their health must do so with an inconvenient and often invasive trip to their health care professional. Moreover, the reliability of data based on, for example, accelerometers, is questionable as they are not able to distinguish between stationary movement and actual steps taken. Accordingly, there is a need for a wearable device that continuously or on demand, provides a wealth of biometric data conveniently and without the need for invasive procedures.

SUMMARY OF THE INVENTION

The present application provides a method, wearable device, and computer readable media for measuring personal health. According to one embodiment, the method includes: detecting a photoplethysmograph (PPG) wave by a personal healthcare device, the PPG waves are generated by infra-red, green or red lights emitted from the personal healthcare device, the personal health care device including an inline sensor (IS) including a first Near Field Infrared (NIR) Light Emitting Diode (LED), a second NIR LED, and a photodiode with wavelength sensitivity range between 900 nm to 1700 nm, the photodiode located on the IS between the first and second NIR LEDs and configured relative thereto to receive reflected light from the first and second NIR LEDs, and a first and second angular mirror, each configured to reflect light from either of the first and second NIR LEDs onto a user's skin and for the user's skin to reflect light back to the photodiode, and the personal healthcare device generates the detected PPG wave based on the light reflected off of the user's skin; transmitting the detected PPG wave to a server that processes the PPG wave and infers therefrom biometric data based on machine learned correlations generated from a training set of PPG waves and biometric data; receiving the biometric data from the server; and generating an interface screen including the biometric data.

In one embodiment, the first NIR LED has a first wavelength in the near infrared spectrum and the second NIR LED has a second wavelength in the near infrared spectrum.

In one embodiment, a first intermediate detected PPG wave is generated from light reflected off of the user's skin from the first NIR LED and a second intermediate detected PPG wave is generated from light reflected off of the user's skin from the second NIR LED, and the detected PPG wave is generated from the combination of the first and second intermediate detected PPG waves.

In one embodiment, the first NIR LED has a wavelength of about 1550 nm±10% and the second NIR LED has a wavelength of about 1300 nm±10%.

In one embodiment, the first NIR LED has a wavelength of approximately 1550 nm and the second NIR LED has a wavelength of approximately 1300 nm.

In one embodiment, light from the first NIR LED is directed to the user's skin via the first angular mirror, and light from the second NIR LED is directed to the user's skin via the second angular mirror, such that the light from the first NIR LED is reflected back off of blood glucose molecules to the photodiode at a first predetermined angle and light from the second NIR LED is reflected back off of blood glucose molecules to the photodiode at a second predetermined angle.

In one embodiment, the first predetermined angle is about 45 degrees and the second predetermined angle is about 90 degrees.

In one embodiment, light from the first and second LEDs is reflected off blood glucose molecules at a depth of about 4 millimeters below the skin surface.

In one embodiment, the inline sensor includes a PCB, and the first and second NIR LEDs, photodiode, and first and second angular mirrors are each attached to the PCB.

In one embodiment, the first and second NIR LEDs are configured to emit light in a direction parallel to the PCB, and the mirrors reflect the emitted light at an oblique angle relative to the PCB.

In one embodiment, the biometric data includes blood glucose levels.

In one embodiment, the server processes the PPG wave and infers therefrom biometric statistics and the biometric statistics includes at least one of overall health, changes in health, mood, sleep quality, fatigue, and stress.

In one embodiment, the machine learned correlations are based on PPG character vectors including a Kaiser-Teager power energy value, a heart rate value, and a spectral entropy value.

In one embodiment, at least one of the mirrors has a single reflective surface.

According to one embodiment, the wearable device includes: a personal healthcare device configured to detect a photoplethysmograph (PPG) wave based on a combination of infra-red and red lights generated from the personal healthcare device. The personal health care device includes: an inline sensor (IS) including a first Near Field Infrared (NIR) Light Emitting Diode (LED), a second NIR LED, and a photodiode with wavelength sensitivity range between 900 nm to 1700 nm, the photodiode located on the IS between the first and second NIR LEDs and configured relative thereto to receive reflected light from the first and second NIR LEDs; a first and second angular mirror, each configured to reflect light from either of the first and second NIR LEDs onto a user's skin and for the user's skin to reflect light back to the photodiode, and the personal healthcare device generates the detected PPG wave based on the light reflected off of the user's skin; a network communication module configured to transmit the detected PPG wave to a server that processes the PPG wave and infers therefrom biometric data based on machine learned correlations generated from a training set of PPG waves and biometric data; a processor configured to generate the biometric data; and an interface screen including the biometric data.

In one embodiment, the server processes the PPG wave and infers therefrom biometric statistics and the biometric statistics includes at least one of overall health, changes in health, mood, sleep quality, fatigue, and stress.

In one embodiment, the machine learned correlations are based on PPG character vectors including a Kaiser-Teager power energy value, heart rate value, and spectral entropy value.

According to one embodiment, the non-transitory computer-readable media includes program code that when executed by a programmable processor causes execution of a method for measuring personal health. The computer-readable media includes: computer program code for detecting a photoplethysmograph (PPG) wave by a personal healthcare device, the PPG waves are generated by infra-red, green or red lights emitted from the personal healthcare device, the personal health care device including the personal health care device including an inline sensor (IS) including a first Near Field Infrared (NIR) Light Emitting Diode (LED), a second NIR LED, and a photodiode with wavelength sensitivity range between 900 nm to 1700 nm, the photodiode located on the IS between the first and second NIR LEDs and configured relative thereto to receive reflected light from the first and second NIR LEDs, and a first and second angular mirror, each configured to reflect light from either of the first and second NIR LEDs onto a user's skin and for the user's skin to reflect light back to the photodiode, and the personal healthcare device generates the detected PPG wave based on the light reflected off of the user's skin; computer program code for transmitting the detected PPG wave to a server that processes the PPG wave and infers therefrom biometric data based on machine learned correlations generated from a training set of PPG waves and biometric data; computer program code for receiving the biometric data from the server; and computer program code for generating an interface screen including the biometric data.

In one embodiment, the server processes the PPG wave and infers therefrom biometric statistics and the biometric statistics includes at least one of overall health, changes in health, mood, sleep quality, fatigue, and stress.

In one embodiment, the machine learned correlations are based on PPG character vectors including a Kaiser-Teager power energy value, a heart rate value, and a spectral entropy value.

BRIEF DESCRIPTION OF THE FIGURES

FIG. 6B is a table of details for light emitting diodes of a flat inline sensor of a personal healthcare device according to one embodiment herein.

DETAILED DESCRIPTION OF THE INVENTION

Figure 1:
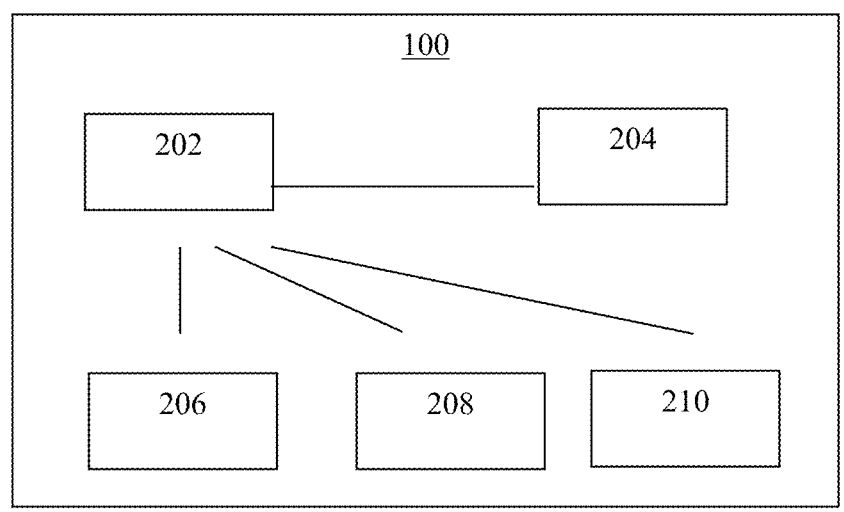
FIG. 1 is a block diagram of a personal healthcare device according to at least one embodiment herein.

Referring to FIG. 1, a wearable personal healthcare device 100 according to at least one embodiment includes a processor 202 coupled to a computer memory 204. The memory stores therein software that when executed causes the device 100 to perform the functions discussed herein. The processor 202 is preferably further coupled to a transmitter/receiver 206 that enables communication between the device 100 and other devices as discussed below. The device 100 preferably includes at least one emitter 208 and one or more sensors 210. The emitter 208 is generally a device that emits energy that is received by sensor 210 in a transformed state. The emitter 208 and sensor 210 are controlled by the processor 202 to emit energy and process the transformed energy, received by the sensor 210 into usable biometric data, as discussed herein. Various types of emitters may be used with the device 100, including light (visible and invisible spectrum), heat, sound, conduction, etc.

The device 100 may include a plurality of each of the emitters/sensors, such as a combination of infra-red and red lights, and corresponding sensors. The device may further include one or more sensors 210 operable to gather hemodynamic and other data which device 100 uses signal processing in processor 202 to reduce the signal noise and then this data is transmitted for further processing remotely into more meaningful parameters such as heart rate, respiratory rate, fat percentage, steps taken, ECG/EKG, blood pressure, body temperature, glucose levels, blood alcohol, blood oxygen, etc. The raw data collected by the device from these sensors 210 may be processed and/or collected remotely on a server to infer, for example, overall health, changes in health, mood, sleep quality, fatigue or stress, etc.

The device 100 is therefore operable to collect data to enable a wealth of personal health data that includes one or more of the following: heart rate, respiratory rate, steps taken, calories burned, distance covered, sleep quality, ECG/EKG, blood pressure, mood, fatigue, body temperature, glucose levels, blood alcohol, blood oxygen, etc. The device 100 may also include one or more of the following features: iPhone/Android connectability, or as a standalone IoT device to allow for remote monitoring of vitals, for example, by a health professional, panic button (that plays audio and visual alarm, communicates GPS position and message to preconfigured address, etc.), accommodate germanium stones, provide a mosquito shield, etc.

The device 100 preferably automatically measures certain biometric data through an internal timer. The rate at which measurements are taken may be preset or set remotely by the wearer, carer or an authorized third party. For example, the rate may be every 30 min, 60 min, etc., selected from a drop-down menu of available rates. The device 100 may further collect data continually, for use, for example, for inferring some of the conclusions therefrom while still displaying and charting the periodic measurements. For example, the device 100 may collect heartrate data continuously and use that to determine heart rate variability, while still only charting hourly measurements. The device 100 may further include sensors that assess biometric data on demand, i.e., when a user elects to take a measurement.

Figure 2:
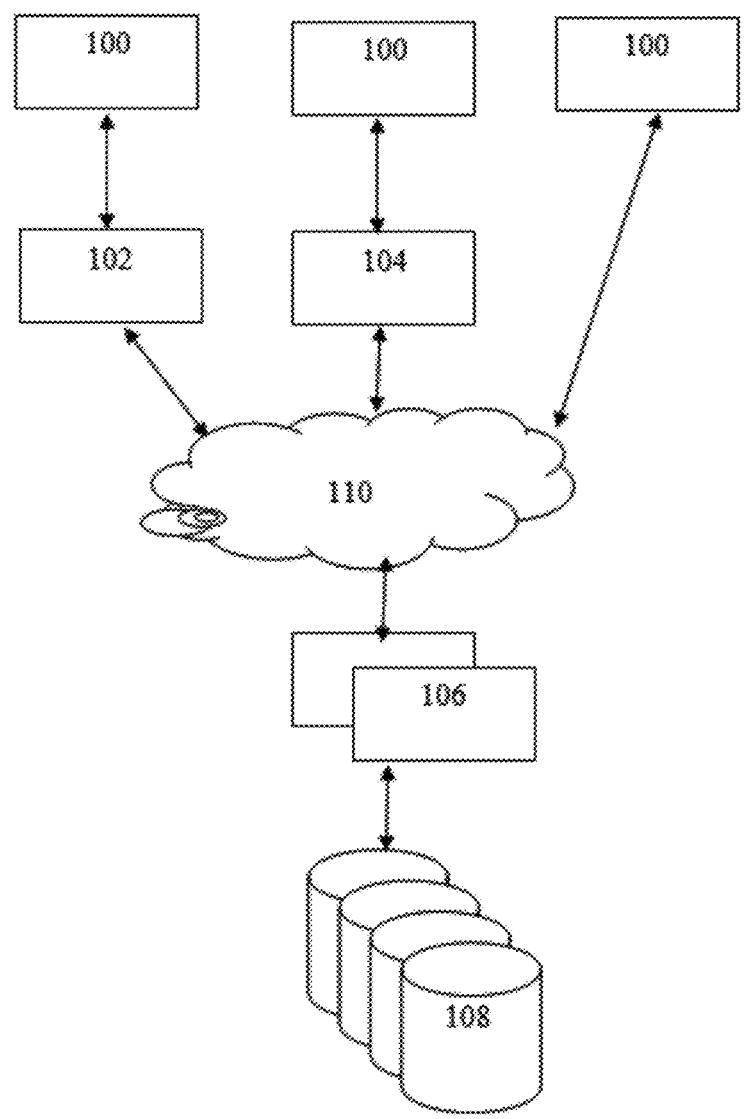
FIG. 2 is a block diagram of a personal healthcare device operating in a network environment according to at least one embodiment herein.

Referring to FIG. 2, the personal healthcare device 100 is preferably operable to communicate with other devices in a network environment. For instance, device 100 may communicate directly with a mobile device 102 (such as a phone or tablet) or a personal computer 104 via a short range wireless connection, such as Bluetooth® or via "Internet of things" (IoT). Additionally, the device 100 may be operable to communicate indirectly with these as well as other devices over a wireless LAN. Finally, the device 100 may operate to provide the functionality discussed herein in conjunction with one or more server computers 106 that are further coupled to one or more databases 108 via the Internet 110.

In at least one embodiment, the device 100 communicates with a mobile device 102 or personal computer 104 that executes an application, which manages the results of the information received from the device 100. The application, for instance, may show current biometric data as well as historic biometric data (collected over time), as shown in FIGS. 8-13. The data may be stored locally on the mobile device 102, personal computer 104, or preferably remotely on the "cloud." With the latter, users can access the data online via a browser application. In another embodiment, the biometric data may be accessed on device 100.

Figure 3:
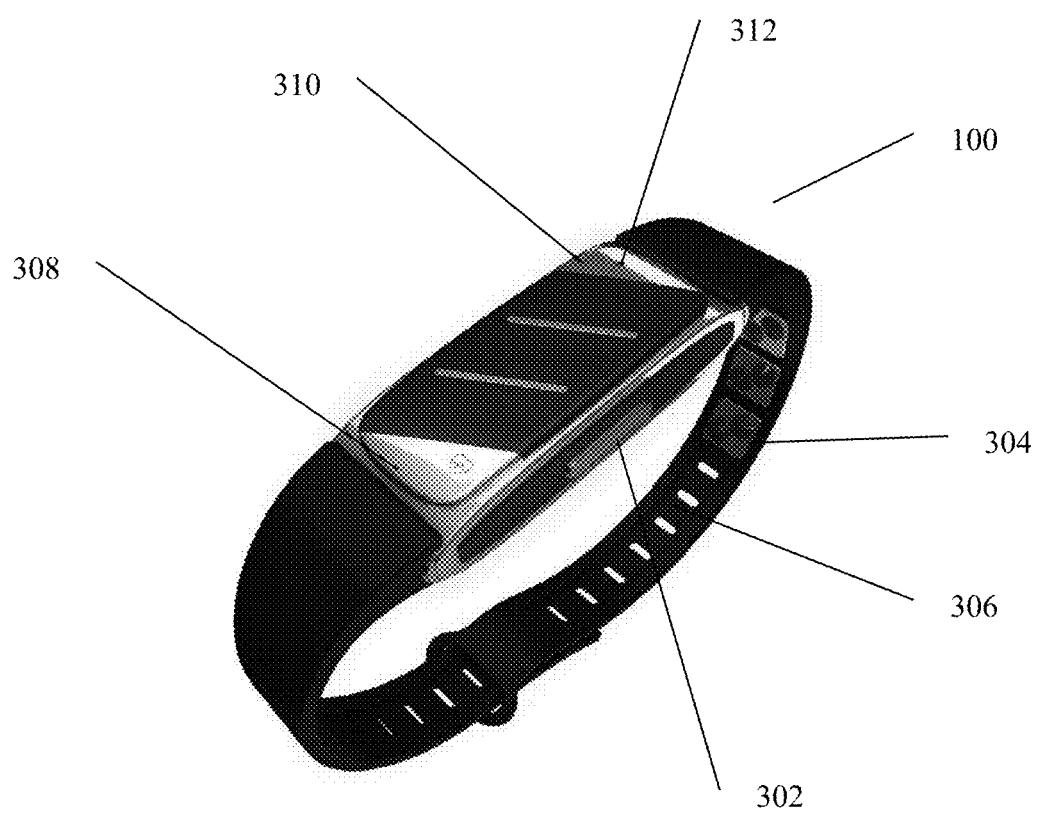
FIG. 3 is a perspective view of a personal healthcare device according to one embodiment herein.
Figure 4:
FIG. 4 is another perspective view a personal healthcare device according to one embodiment herein.
Figure 5:
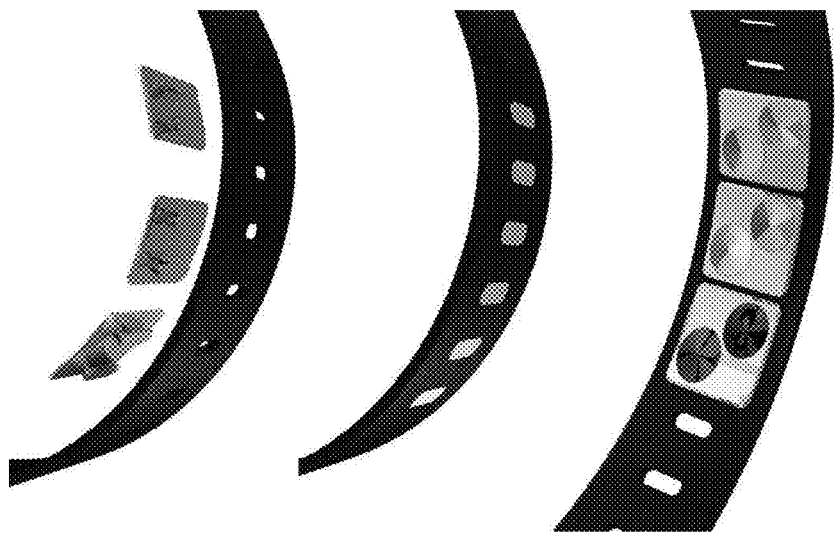
FIG. 5 are a set of views of the wrist band for a personal healthcare device according to one embodiment herein.

Referring to FIG. 3, in one embodiment, the device 100 is in the form of a device that is worn on the user's wrist. In this regard, the device 100 may include a wrist band with ends that are detachably connected to each other. The device 100 may further include a mode button 302 that when pressed for a present amount of time toggles through certain functionality. For instance, 2 seconds may turn the device 100 on, whereas 8 seconds may turn the device off. The succession of clicks may trigger other functionality, such as double select to trigger the panic button functionality. The device 100 may also include a display 312, which may be a simple LED or something more robust such as an LCD that displays textual/numeric biometric data. In one embodiment, the device 100 includes a first and/or second sensors 308, 310 on the outer face of the device 100. For instance, the device may include a bioelectric impedance sensor 308. These sensors may also be on the bottom side, as shown in FIG. 4 (402, 404). Moreover, top and bottom sensors may be used in which the user touches a top sensor 308, e.g., with a finger, to compete the circuit with a bottom sensor 402 to gather additional data which enables EKG to be deduced in near real-time. Finally, the device 100 may include a unique mechanism for attaching stones 304 directed to the wearers skin. The stones are preferably installed on modular platforms that allow them to be interchangeably added to the wrist band of the device, as shown in FIG. 5.

Figure 6A:
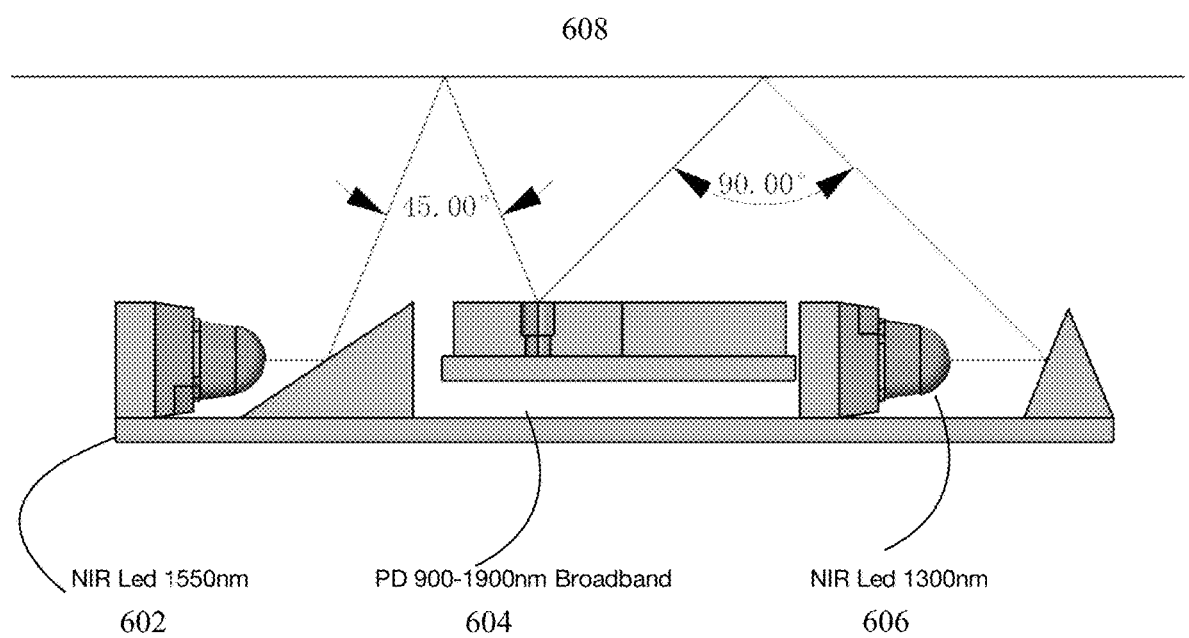
FIG. 6A is an illustration of a flat inline sensor of a personal healthcare device according to one embodiment herein.

According to another embodiment a flat inline sensor (FIS), as illustrated in FIG. 6A may be used. The FIS may be mechanically applied adjacent to the body where there are blood vessels below, it is possible to obtain valid Photoplethysmography (PPG) signals at different frequencies which can be used to determine glucose levels in these blood vessels. The FIS may be a Surface Mounted Device (SMD) Package type that includes 1 Near Field Infrared (NIR) LED with Wave length of 1300 nano meter (nm) (606), 1 NIR LED with Wave length of 1550 nm (602) and one Photodiode (PD) with broad range wavelength sensitivity between 900 nm to 1700 nm (604). Light from the two NIR LEDs is directed to the skin 608 via two angular mirrors, ensuring that the light reflecting back is at a predetermined angle as shown in the diagram, when it is captured by the PD. Using PPG techniques and 2 specific NIR LEDs at very high frequency wavelength (1300 and 1550 nm) in a specific configuration, high frequency wavelength light is reflected at specific angles when it is reflected off blood glucose molecules. e.g., 90 degree for light of a wavelength of 1550 nm and 45 Degrees for the 1300 nm.

FIG. 6B outlines the details of four Light Emitting Diodes, including specification and function (e.g., capturing data to enable Heart Rate, Blood Oxygen Levels and Blood Sugar to be deduced) that may be used in the FIS.

Figure 6C:
FIG. 6C is a table of details for photodiodes of a flat inline sensor of a personal healthcare device according to one embodiment herein.

FIG. 6C outlines details of exemplary photodiodes that may be used in the FIS.

Figure 6D:
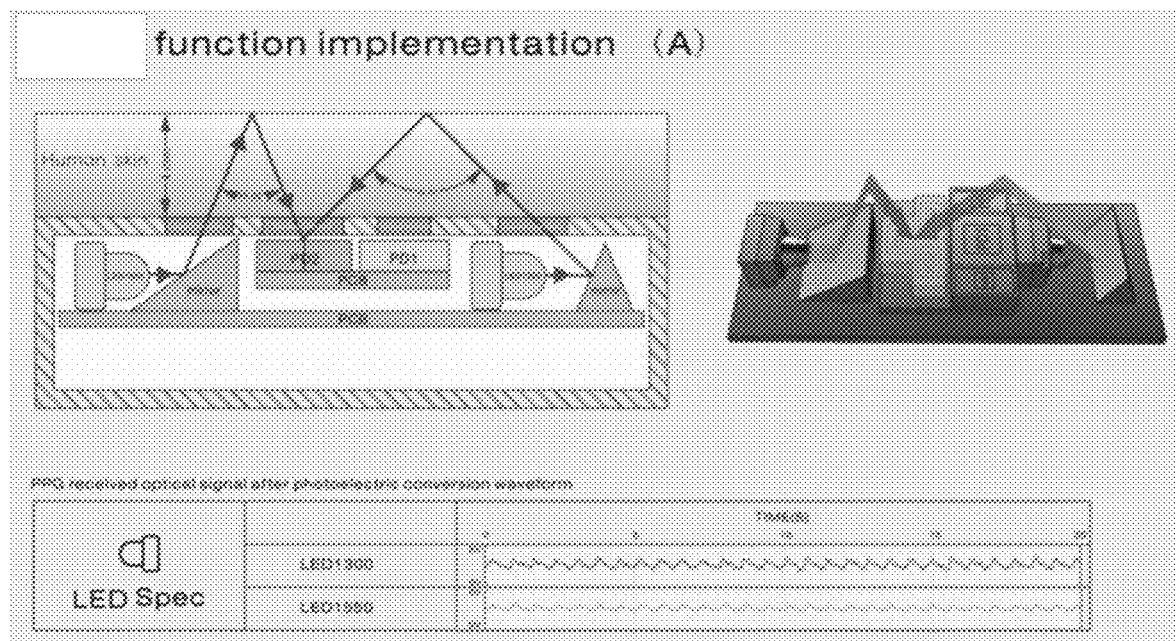
FIG. 6D is an illustration of functional implementation of a flat inline sensor of a personal healthcare device according to one embodiment herein.

FIG. 6D displays functional implementation of the FIS adjacent to skin for LED 1300 and LED1550 as the light is reflected at a depth of some 4 mm below the skin. The first angle is 45 degrees and the wider angle is 90 degrees.

Figure 6E:
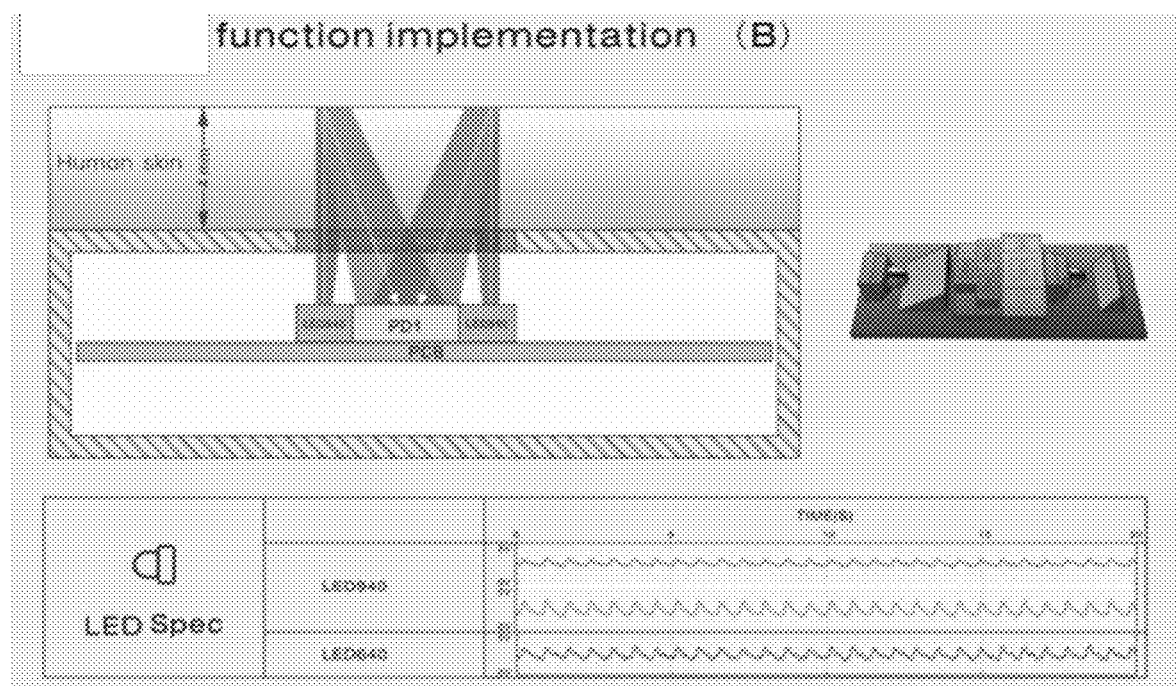
FIG. 6E is an illustration of another functional implementation of a flat inline sensor of a personal healthcare device according to one embodiment herein.

FIG. 6E displays the functional implementation of the FIS adjacent to skin for LED940 and LED640 as the light is reflected at a depth of some 4 mm below the skin.

Referring back to FIG. 4, the bottom or underside of the device 100 is shown. This side may include one or more sensors thereon, 402, 404, etc. The bottom of the device 100 preferably include a plurality of sensors, include at least a synchronous red light and near infrared light emitters/sensors. Referring to FIG. 5, the details of the wristband are shown. Specifically, the band includes a plurality of apertures, equally spaced to accommodate the pedestals having stones thereon. The cross section of the apertures is preferably hourglass shaped to retain similarly shaped legs on the pedestal. The pedestals are inserted from the inside of the band through the apertures therein. The pair of legs of the pedestals fit flush with the outside of the band, as shown. The tops of the pedestals include therein at least one stone. A stone is generally a material that is believed to have beneficial properties, such as gold, silver, copper, germanium, magnets, salt, etc. The pedestals beneficially bring the stones into contact with the wearers skin.

Figure 7:
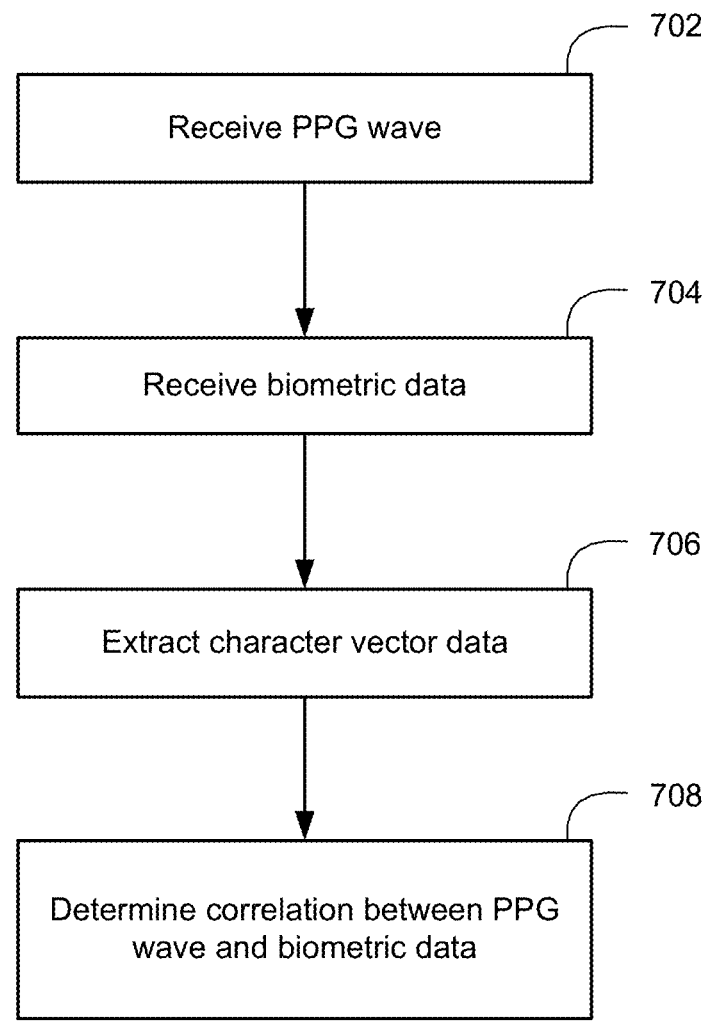
FIG. 7 is a flowchart of a method for training a learning machine to interpret data from a personal healthcare device according to one embodiment herein.

FIG. 7 presents a flowchart of a method for training a learning machine to interpret data from a personal healthcare device according to one embodiment herein according to one embodiment herein. In at least one embodiment, the device 100 employs synchronous red light and near infrared light to generate a photoplethysmograph (PPG) wave that is analyzed to determine a biometric measure, such as blood glucose level (BGL) or any of the other biometrics discussed herein. A PPG wave is received by an analytical server from the device 100, step 702. The steps in assessing biometrics using PPG may be premised on the correlation between PPG and BGL, blood pressure, etc. Similarly, the correlation between PPG and key nutrition element and/or blood vessel endothelium health status may also be analyzed.

This analysis may be achieved by sampling, for example, 1000 persons for PPG wave data, standard BGL, blood pressure, etc., to produce training data for machine learning. The test may be undertaken, for example, before breakfast every day for 14 consecutive days.

The algorithms for determining BGL and other biometrics from PPG data may be derived with the following exemplary process:

Obtaining biometric data—biometric data is received, step 704—using, for example, a personal healthcare device with a flat inline sensor or a specified fingertip clip device with 660 nm red light and 940 nm near infrared light to get PPG data, the device may take 2 readings allowing 1 minute for each reading. Then the BGL may be tested using a medical level micro trauma blood glucose monitor. Blood pressure may also be taken with a cuff sphygmomanometer, again ensuring that two readings are taken. For each person, the test will continue for 2 weeks, 2 times every day around the same time each day with the first time in the morning before breakfast and the second time in the afternoon, 1 hour after eating lunch. A person's sex, age, height, weight, country, ethnicity, cardiovascular and cerebro-vascular diseases history, metabolism diseases history, family diseases history, continuo and any ongoing medication or history of medical conditions may be provided along with the biometric data. The location, amount of caffeine taken, smoking and if so, to what extent, emotion, fatigue and so on may also be recorded.

The PPG data generated may be processed to get the clean signal. Character vector data is extracted, step 706—the PPG wave may be filtered with a band pass filter, allowing waves of about 0.5 Hz to about 5 Hz and then an adaptive noise canceller may be applied using the RLSL (recursive least squares) method. The key to usable data is to find the effective reference signal and extract the character vectors. From the clean signal, character vectors may be distinguished and extracted, and then supervised machine learning may be applied to compute a correlation. The resulting formula may be assessed against a subset of the test data to predict validity of the algorithm.

Exemplary PPG character vectors:

Kaiser-Teager power energy value: $KTE_n = x(n)^2 - x(n+1) x(n-1)$, where x is the electromyographic value and n is the sample number, segmented real-time power energy value: $KTE_n$, mean value $KTE_n^\mu$, mean square deviation $KTE_n^\sigma$, quarter distance $KTE_n^\alpha$, slewness $KTE_n^\beta$, and corresponding segments $KTE^\mu$, $KTE^\sigma$, $KTE^\alpha$, $KTE^\beta$ may be obtained.

Heart rate value: from the PPG wave, the corresponding $HRP^\mu$, $HR^\sigma$, $HR^\alpha$, $HR^\beta$ may be computed.

Spectral entropy can be useful and to be considered, for determining the FFT (fast Fourier transform) for the segmented signal, means $X_n \leftarrow FFT(x(n), L)$, followed regularization. Knowing the probability mass function $P_x^n$, then the entropy may be computed, $H \leftarrow Px^n \text{Log}(Px^n)$. The segmented data may be: $H_n^\mu$, $H_n^\sigma$, $H_n^\alpha$, $H_n^\beta$. If computing overflow happens, conduct log function, $\text{Log } E \leftarrow \text{Log}(x(n))$, knowing $\text{Log } E^\sigma$ and $\text{Log } E^\alpha$.

Red light and near infrared light peak values, Pr, Pi may also be computed independent of the power value. To avoid the respiratory impact, the segmented time duration can be 5 s to 10 s, the signal is x(n), and the corresponding matrix is Xi. When conducting this computation, new valid vector elements may be added and trivial impact signals removed.

A correlation between PPG wave and biometric data may be determined using supervised machine learning, step 708. The vector dimension may be from 10 to 20 from the PPG data. Randomly, 90% of the data may be placed into training set, another 10% into the test set. A machine learning algorithm can be used to compare: least square method linear recursive compute, logistic recursive compute, support vector machine (SVM), classification and regression trees (CART), random forest, neural network (NN), AdaBoost, and so on. SVM may use SMO (Sequential Minimal Optimization) and kernel function, using the radial basis function as kernel function. The NN may be BP (back propagation) and Hopfield to do the test. Based on the training and testing via machine learning, certain aspects of the biometric data may be correlated with certain PPG waves.

Figure 8:
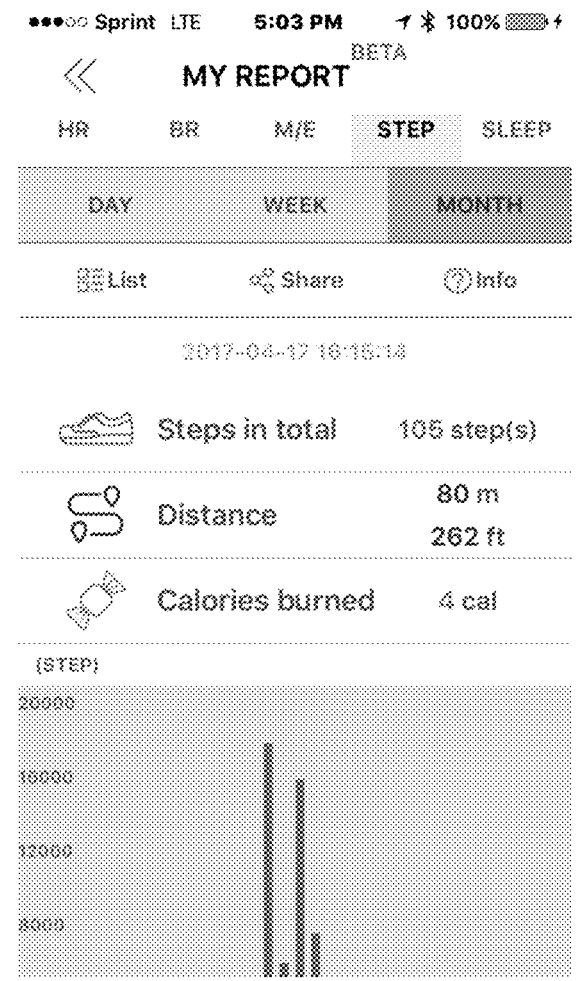
FIGS. 8-13 are a set of interface screens displayed on a mobile device app associated with the personal healthcare device according to one embodiment herein.

FIG. 8 presents an interface screen for displaying step data of a user that is determined from a personal healthcare device according to one embodiment herein. The interface may include step data according to a daily, weekly, or monthly basis. The personal healthcare device may record an amount of total steps, distance, and calories burned. The amount of steps may also be provided in a chart over a given period.

Figure 9:
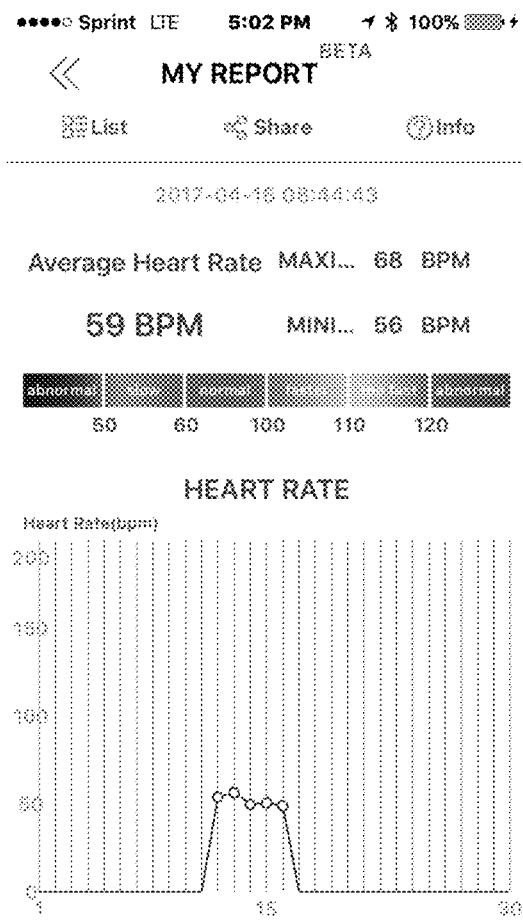

FIG. 9 presents an interface screen for displaying heart rate data of a user that is determined from a personal healthcare device according to one embodiment herein. The interface may include a record of maximum and minimum of beats per minute along with a guideline range of normal/abnormal heart rate. The heart rate interface may further calculate a user's average heart rate and chart the user's heartrate over a given period.

Figure 10:

FIG. 10 presents an interface screen for displaying respiratory rate data of a user that is determined from a personal healthcare device according to one embodiment herein. The interface may present a determined respiratory rate (times per minute) for a user as determined by the personal healthcare device. The determined respiratory rate of the user may be charted over a given period.

Figure 11:
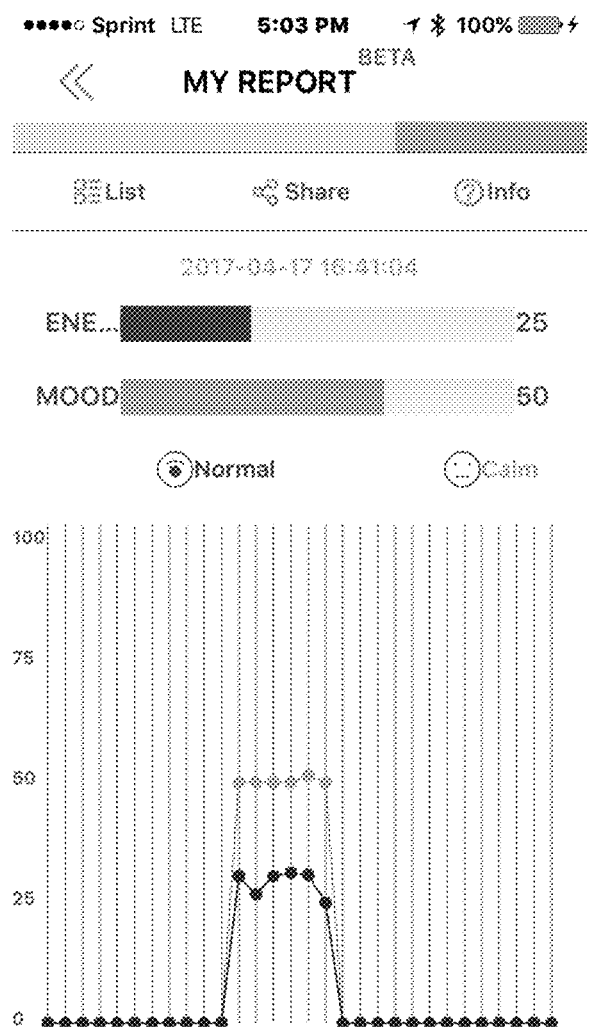

FIG. 11 presents an interface screen for displaying energy and mood data of a user that is determined from a personal healthcare device according to one embodiment herein. Energy and mood of a user may be calculated according to a predetermined scale. For example, an energy level of '25' may be normal and mood of '50' may indicate that the user is calm. Energy and mood may be charted over a given period.

Figure 12:
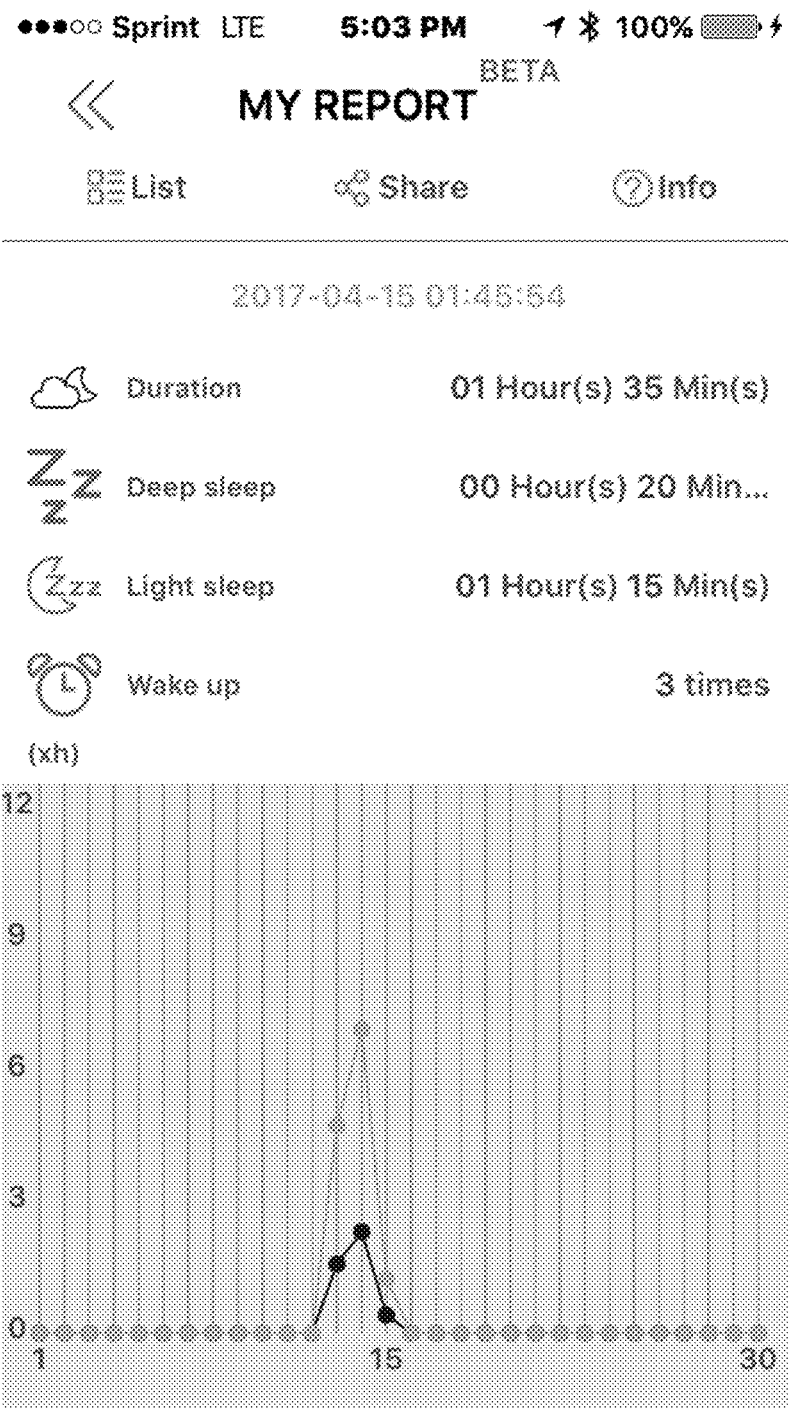

FIG. 12 presents an interface screen for displaying sleep data of a user that is determined from a personal healthcare device according to one embodiment herein. Sleep data may include total sleep duration, duration of deep sleep, duration of light sleep, and how many times during sleep did the user wake up. One or more data points for sleep may be plotted on a chart over a given period.

Figure 13:
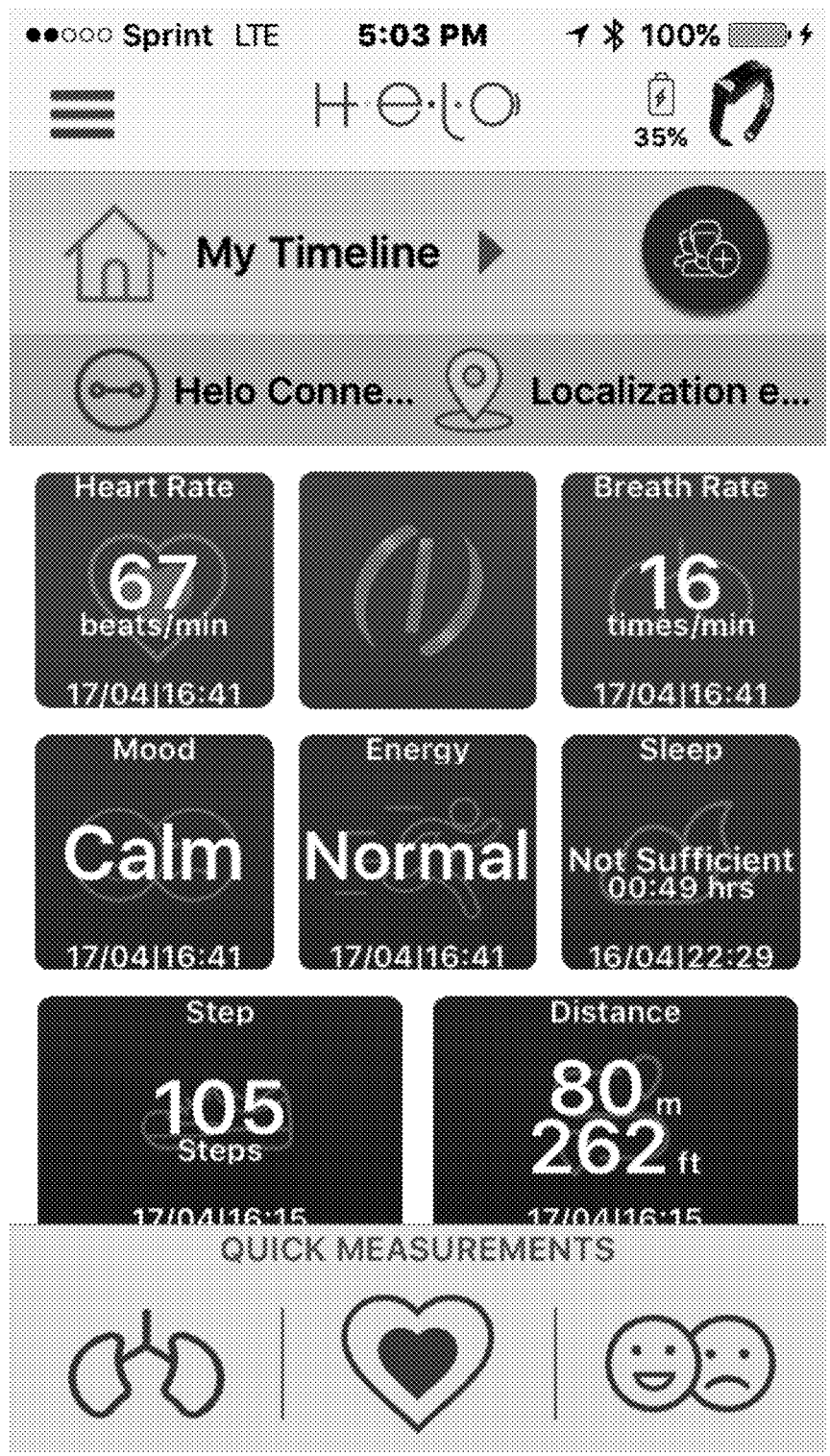

FIG. 13 presents an exemplary home screen of a personal healthcare device according to one embodiment herein. The home screen may include a quick summary of the data described with respect to FIGS. 8-12. Each data category may be presented in selectable tiles that can be expanded to display the data in detail. Additionally, the home screen may provide a feature to take "quick measurements" of respiratory rate, heart rate, energy and mood, for example.

While the foregoing invention has been described in some detail for purposes of clarity and understanding, it will be appreciated by one skilled in the art, from a reading of the disclosure, that various changes in form and detail can be made without departing from the true scope of the invention.

What is claimed is:

1. A method, in a data processing system comprising a processor and a memory, for measuring personal health, the method comprising:
   detecting a photoplethysmograph (PPG) wave by a personal healthcare device, the PPG waves are generated by lights emitted from the personal healthcare device, wherein the personal health care device comprises:
   an inline sensor (IS) comprising a first Light Emitting Diode (LED), a second LED, and a photodiode, the photodiode located on the IS between the first and second LEDs and configured relative thereto to receive reflected light from the first and second LEDs, and a first and second angular mirror, each configured to reflect light toward a user's skin and for the user's skin to reflect light back to the photodiode, wherein light from the first LED is directed to the user's skin via the first angular mirror, and light from the second LED is directed to the user's skin via the second angular mirror, such that the light from the first LED is reflected back off of blood glucose molecules to the photodiode at a first predetermined angle and light from the second LED is reflected back off of blood glucose molecules to the photodiode at a second predetermined angle, wherein the personal healthcare device generates the detected PPG wave based on the light reflected off of the user's skin;

transmitting the detected PPG wave to a server, wherein the server processes the PPG wave and infers therefrom biometric data;

receiving the biometric data from the server; and generating an interface screen comprising the biometric data.

2. The method of claim 1, wherein the first LED has a first wavelength in the near infrared spectrum and the second LED has a second wavelength in the near infrared spectrum.

3. The method of claim 1, wherein a first intermediate detected PPG wave is generated from light reflected off of the user's skin from the first LED and a second intermediate detected PPG wave is generated from light reflected off of the user's skin from the second LED, and the detected PPG wave is generated from the combination of the first and second intermediate detected PPG waves.

4. The method of claim 1, wherein the first Previously Presented LED has a wavelength of about 1550 nm±10% and the second LED has a wavelength of about 1300 nm±10%.

5. The method of claim 1, wherein the first LED has a wavelength of approximately 1550 nm and the second LED has a wavelength of approximately 1300 nm.

6. The method of claim 1, wherein the first predetermined angle is about 45 degrees and the second predetermined angle is about 90 degrees.

7. The method of claim 1, wherein light from the first and second LEDs is reflected off blood glucose molecules at a depth of about 4 millimeters below the skin surface.

8. The method of claim 1, wherein the inline sensor further comprises a PCB, and the first and second LEDs, photodiode, and first and second angular mirrors are each attached to the PCB.

9. The method of claim 8, wherein the first and second LEDs are configured to emit light in a direction parallel to the PCB, and wherein the mirrors reflect the emitted light at an oblique angle relative to the PCB.

10. The method of claim 1, wherein the biometric data comprises blood glucose levels.

11. The method of claim 1, wherein the server processes the PPG wave and infers therefrom biometric statistics and wherein the biometric statistics comprise at least one of overall health, changes in health, mood, sleep quality, fatigue, and stress.

12. The method of claim 1, wherein at least one of the mirrors has a single reflective surface.

13. The method of claim 1, wherein the photodiode has a wavelength sensitivity range between 900 nm to 1700 nm.

14. The method of claim 1, wherein the first LED has a first wavelength in the red or near infrared spectrum, the second LED has a second wavelength in the red or near infrared spectrum, and the photodiode has a wavelength sensitivity range in the red or near infrared spectrum.

15. A wearable device for measuring personal health comprising:

a personal healthcare device configured to detect a photoplethysmograph (PPG) wave based on a combination of lights generated from the personal healthcare device, the personal health care device comprising:

an inline sensor (IS) comprising a first Light Emitting Diode (LED), a second LED, and a photodiode, the photodiode located on the IS between the first and second LEDs and configured relative thereto to receive reflected light from the first and second LEDs;

a first and second angular mirror, each configured to reflect light toward a user's skin and for the user's skin to reflect light back to the photodiode, wherein light from the first LED is directed to the user's skin via the first angular mirror, and light from the second LED is directed to the user's skin via the second angular mirror, such that the light from the first LED is reflected back off of blood glucose molecules to the photodiode at a first predetermined angle and light from the second LED is reflected back off of blood glucose molecules to the photodiode at a second predetermined angle, wherein the personal healthcare device generates the detected PPG wave based on the light reflected off of the user's skin;

a network communication module configured to transmit the detected PPG wave to a server, wherein the server processes the PPG wave and infers therefrom biometric data;

and an interface screen configured to display the biometric data.

16. The wearable device of claim 15 wherein the server processes the PPG wave and infers therefrom biometric statistics and wherein the biometric statistics comprise at least one of overall health, changes in health, mood, sleep quality, fatigue, and stress.

17. The wearable device of claim 15, wherein the photodiode has a wavelength sensitivity range between 900 nm to 1700 nm.

18. A wearable device for measuring personal health comprising:

a personal healthcare device configured to detect a photoplethysmograph (PPG) wave based on a combination of lights generated from the personal healthcare device, the personal health care device comprising:

an inline sensor (IS) comprising a PCB, a first Light Emitting Diode (LED), a second LED, a photodiode, and a first and second angular mirror, wherein the first and second LEDs, photodiode, and first and second angular mirrors are each attached to the PCB, the photodiode is located on the IS between the first and second LEDs and configured relative thereto to receive reflected light from the first and second LEDs;

and the first and second angular mirror are each configured to reflect light from either of the first and second LEDs toward a user's skin and for the user's skin to reflect light back to the photodiode, wherein the personal healthcare device generates the detected PPG wave based on the light reflected off of the user's skin;

a network communication module configured to transmit the detected PPG wave to a server, wherein the server processes the PPG wave and infers therefrom biometric data; and an interface screen configured to display the biometric data.

19. The wearable device of claim 18, wherein the first and second LEDs are configured to emit light in a direction parallel to the PCB, and wherein the mirrors reflect the emitted light at an oblique angle relative to the PCB.

20. The wearable device of claim 18, wherein the first LED has a first wavelength in the near infrared spectrum, the second LED has a second wavelength in the near infrared spectrum, and the photodiode has a wavelength sensitivity range between 900 nm to 1700 nm.

\* \* \* \* \*